United States Patent [19]

Strausburg

[11] 4,269,119

[45] May 26, 1981

[54] SETTING KNOBS FOR SELECTIVE PRINT HEAD

[75] Inventor: Larry D. Strausburg, Miamisburg, Ohio

[73] Assignee: Monarch Marking Systems, Inc., Dayton, Ohio

[21] Appl. No.: 70,377

[22] Filed: Aug. 27, 1979

[51] Int. Cl.3 .......... A61B 5/12; B41J 1/20

[52] U.S. Cl. .......... 101/111; 74/553; 74/554; 16/121

[58] Field of Search .......... 101/110, 111; 74/552, 74/553, 554, 10 R, 10.2, 10.45; 403/11, 109, 112, 359; 16/115, 121, DIG. 39, DIG. 41

[56] References Cited

U.S. PATENT DOCUMENTS

| | | | |
|---|---|---|---|
| 2,111,965 | 3/1938 | Crutchfield | 16/121 |
| 2,901,920 | 9/1959 | Felts | 74/554 X |
| 3,100,404 | 8/1963 | Boeddeker et al. | 74/553 |
| 3,557,637 | 1/1971 | Tomczak | 74/553 |
| 3,948,172 | 4/1976 | Jenkins | 101/316 |
| 4,132,129 | 1/1979 | Pratt | 74/553 |

FOREIGN PATENT DOCUMENTS

| | | | |
|---|---|---|---|
| 2701017 | 7/1978 | Fed. Rep. of Germany | 74/554 |

*Primary Examiner*—Edward M. Coven
*Attorney, Agent, or Firm*—Joseph J. Grass

[57] ABSTRACT

There is disclosed a multi-line print head for a labeler. The print head includes a plurality of lines of printing members and a selector for each line. Each selector includes a shaft rotatable by a respective knob. The knobs are close to each other in certain axial positions. Each knob can transmit rotation and axial movements to its respective shaft. However, any knob can be shifted axially to a limited extent relative to its respective selector shaft to a position clear of any other knob. Thus, the other knob or knobs do not interfere with manual rotation of the selected knob.

10 Claims, 8 Drawing Figures

FIG-1
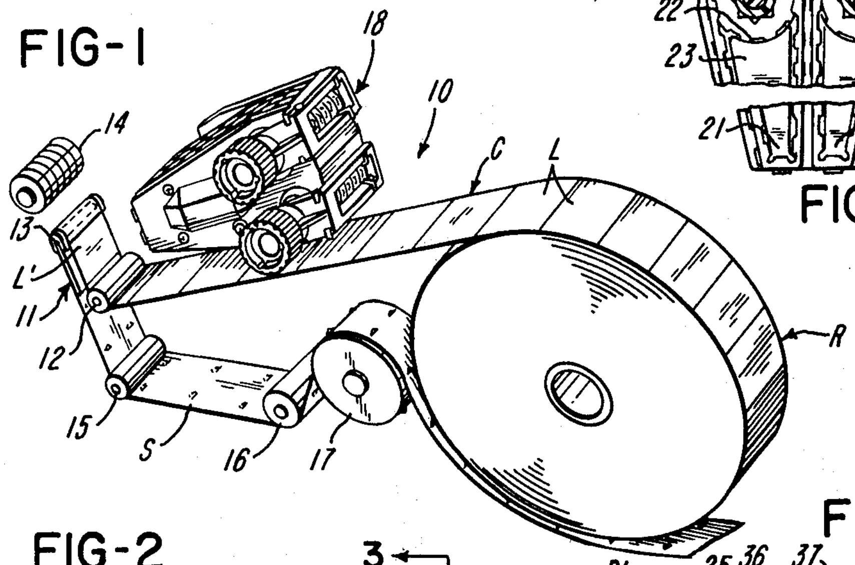
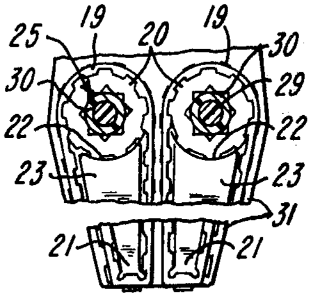
FIG-8
FIG-2
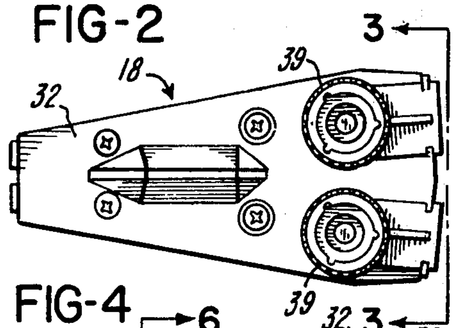
FIG-3
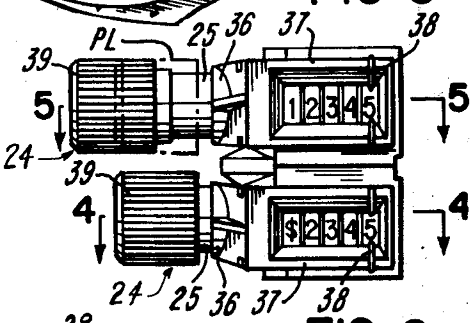
FIG-4
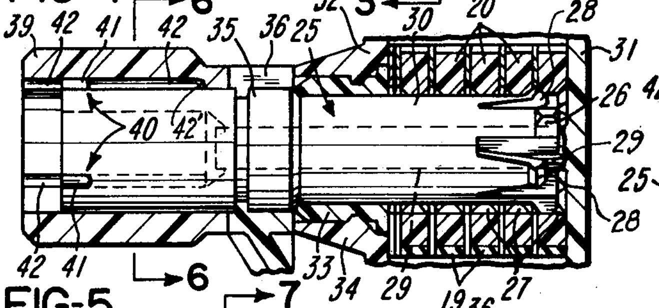
FIG-6
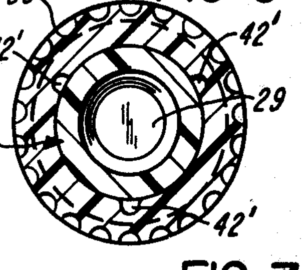
FIG-5
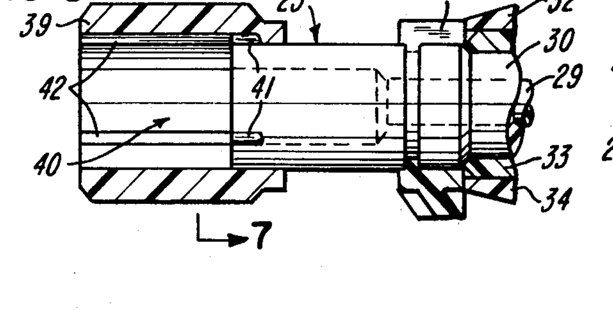
FIG-7
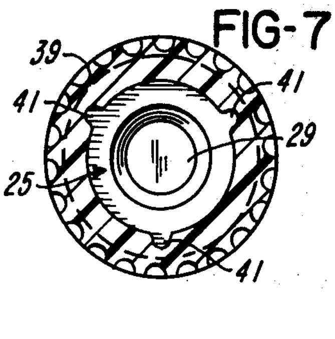

SETTING KNOBS FOR SELECTIVE PRINT HEAD

BACKGROUND OF THE INVENTION

1. Field of the Invention

This invention relates to the art of print heads.

2. Brief Description of the Prior Art

A prior art U.S. patent disclosing a multi-line print head having a plurality of selectors for selectively setting two lines of data is U.S. Pat. No. 3,948,172 granted Apr. 6, 1976 to William A. Jenkins.

SUMMARY OF THE INVENTION

This invention relates to a print head having two or more lines of selectable printing members. A manually shiftable and rotatable selector shaft is used to accomplish selection. It is desirable to keep the overall size of print heads to a minimum. One reason is to avoid stage printing. Another reason is that the size of the print head affects the overall size of a hand-held labeler. In providing a compact, small size, print head it is difficult to manually rotate the closely spaced selector knobs because of interference with one or more adjacent selector knobs. The present invention overcomes this problem. According to one embodiment of the invention, each selector shaft is rotated and shifted by means of a respective knob and there is a lost-motion connection between the knob and its respective selector shaft so that any knob can be shifted axially on the selector shaft. The knob telescopes in the axial direction within limits but drives the shaft when the knob is rotated by the user. In the illustrated embodiment the knob and selector shaft are coupled by means of a spline. In that the knob and selector shaft are non-circular, rotation of the knob transmits rotational force directly to the selector shaft. Movement of any knob in the axial direction relative to its shaft is limited by cooperable stop means on the selector shaft and the respective knob. The knob can also shift the selector shaft axially.

BRIEF DESCRIPTION OF THE DRAWINGS

FIG. 1 is a diagrammatic perspective view of a label printing and applying apparatus incorporating the print head of the invention;

FIG. 2 is a side elevational view of the print head;

FIG. 3 is a view taken along line 3—3 of FIG. 2;

FIG. 4 is a fragmentary sectional view taken generally along line 4—4 of FIG. 3;

FIG. 5 is a fragmentary sectional view taken generally along line 5—5 of FIG. 3;

FIG. 6 is a sectional view taken along line 6—6 of FIG. 4;

FIG. 7 is a sectional view taken along line 7—7 of FIG. 5; and

FIG. 8 is a fragmentary sectional view through the print head.

DETAILED DESCRIPTION OF THE PREFERRED EMBODIMENT

With reference to FIG. 1, there is shown a label printing and applying apparatus generally indicated at 10 for printing on a composite web C of labels L carried on a web of supporting material S. The composite web C is carried in the form of a roll R and passes to a printing position 11 about a guide roller 12. The leading label L' undergoes a sharp change in direction at a delaminator 13 from which the leading label L' passes into label applying relationship with respect to an applicator 14 shown to be a roll. From there the supporting web S is guided by rollers 15 and 16 into engagement with a toothed driver or feed wheel 17. When the driver 17 is rotated in the clockwise direction the supporting material S is advanced and the leading label L' is delaminated from the supporting web S at the delaminator 13.

It is a feature of the invention to provide a multi-line print head generally indicated at 18 having a plurality of lines of printing members which, in the illustrated embodiment, are shown to be printing bands 19. Each printing band is trained under tension about a respective drive wheel 20 and a support 21. The drive wheels 20 are mounted at their outer peripheries on concave mounting surfaces 22 of mounting blocks 23. Each support 21 is preferably integral with the respective mounting block 23 but idler wheels (not shown) can be used if desired. The drive wheels 20 have small diameters and hence their axes can be relatively close together. As best shown in FIG. 4, a selector 24 includes a selector shaft 25. The shaft 25 is shown to have at least one drive lug 26 which is engageable in a corresponding notch 27 of any wheel 20. At least one detent element 28 is shown to be in detenting relationship between adjacent wheels 20. A central post 29 is shown to extend into and guide a tubular portion 30 of the selector shaft 25. The post 29 is connected to a side plate 31. Another side plate 32 is disposed at the other side of the print head 18 so that the bands 19, wheels 20, and the supports 21 are disposed between side plates 31 and 32. A bushing 33 disposed within tubular portion 34 of the side plate 32 slidably guides the tubular portion 30 of the selector shaft 25. The selector shaft 25 also has an enlarged annular portion 35 about which a split collar 36 is received. The collar 36 carries a pointer or indicator 37. The indicator 37 includes an indicator element 38 which points to the selected printing band 19. The tooth 26 is engaged with the selected wheel 20 which in turn is coupled to the selected printing band 19.

Each selector 24 also includes a knob 39. The selector shaft 25 is shown to be connected to the knob 39 by a lost-motion connection generally indicated at 40. As illustrated, both the outer periphery of the shaft 25 and the inner periphery of the knob 39 are non-circular. More specifically, the knob 39 is splined with the selector shaft 25 by splines or projections 41 received in grooves 42. The splines 41 on the shaft 25 engage with grooves 42 in the knob 30 to cause rotation of the shaft 25 when the knob 39 is rotated in either direction. However, the splines 41 enable the knob 39 to shift axially relative to the selector 25 as best illustrated with reference to FIG. 4 and 5. The splines 41 are relatively short and thus provide abutments or stops when the knob 39 has undergone a predetermined amount of travel as illustrated in FIG. 5. The shaft 25 can be shifted to the left in FIG. 5, that is, outwardly by pulling on the knob 39 because splines or projections 41 engage stop shoulders 42'. The shaft 25 can be moved inwardly by the knob 39 when the knob 39 is in abutment with collar 36. Thus, the knob 39 can be moved freely within limits and when the limits are reached the knob 39 starts transmitting axial movement to the selector shaft 25.

It is preferred that the printing bands 19 have printing positions and non-printing human-readable portions. With reference to FIG. 3, both of the selector shafts 25 are shown to be positioned so that their respective lugs 28 are coupled to the endmost printing bands 19 in which the character 5 of the human-readable portion is visible and the printing element for printing character 5 is at the printing position. It is apparent that the knob 39 associated with the one line of printing is shown to have been pulled out to the maximum position from the position indicated by phantom lines PL. In this position, the pulled-out knob 39 (upper knob in FIG. 3) can be rotated without the other knob 39 (lower knob in FIG. 3) interfering or getting in the way. Nevertheless, any one of the shafts 25 can be shifted axially and rotated to advance a printing band 19.

If desired, the knobs 39 can be constructed (as by molding) using flexible resilient material so that the user can pinch any knob 39 to clutch the knob 39 to the selector shaft 25 to override the effect of the lost-motion connection between the knob 39 and the selector shaft 25.

It is apparent that the invention is also applicable to print heads having three or more settable lines.

Other embodiments and modifications of this invention will suggest themselves to those skilled in the art, and all such of these as come within the spirit of this invention are included within its scope as best defined by the appended claims.

I claim:

1. A print head, comprising: a plurality of lines of printing members for printing a plurality of lines of data, an axially shiftable and rotatable selector shaft for each line of printing members for selectively advancing any printing member in its line, a manually engageable knob mounted on each selector shaft for both rotating the selector shaft and axially shifting the selector shaft, each knob being non-rotatably mounted relative to the related selector shaft, adjacent knobs being relatively close to each other in certain axial positions, and means providing a lost-motion connection between each knob and its respective selector shaft to enable the knob to be pulled outwardly in the axial direction to a limited extent relative to any other knob to reduce interference with any other knob.

2. A print head, comprising: a plurality of lines of printing members for printing a plurality of lines of data, an axially shiftable and rotatable selector shaft for each line of printing members for selectively advancing any printing member in its line, each shaft having a non-circular portion, manually engageable knobs for shifting and rotating the respective shafts, each knob being non-rotatably mounted relative to the related selector shaft and having a non-circular portion engaged with a respective non-circular shaft portion to enable the knob to rotate the shaft, adjacent knobs being relatively close to each other in certain axial positions, each knob being axially slidably mounted on the respective shaft to enable any knob to be shifted axially outward to a limited extent relative to its shaft to reduce interference with any other knob.

3. A print head, comprising: a plurality of lines of printing members for printing a plurality of lines of data, an axially shiftable and rotatable selector shaft for each line of printing members for selectively advancing any printing member in its line, manually engageable knobs for shifting and rotating the respective shafts, adjacent knobs being relatively close to each other in certain axial positions, and a spline connection between each knob and its respective shaft for enabling the knob to be shifted axially relative to the shaft to a position where interference with any other knob is reduced and for enabling each knob to shift and to rotate its respective selector shaft.

4. A print head as defined in any of claims 1, 2 or 3 including stop means for limiting movement of each knob in the axial direction.

5. A print head, comprising: a plurality of lines of drive wheels, each drive wheel having a hole, means for rotatably mounting the drive wheels of each line, a plurality of lines of printing bands engaged with the wheels for printing a plurality of lines of data, an axially shiftable and rotatable selector shaft movable into the wheel holes of each line for selectively engaging any wheel to advance the respective printing band, a manually engageable knob non-rotatably mounted on each selector shaft for rotating and shifting the shaft axially, and means providing a lost-motion connection between each knob and its respective selector shaft to enable the knob to be pulled outwardly in the axial direction relative to any other knob to reduce interference with any other knob.

6. A print head, comprising: a plurality of lines of drive wheels, each drive wheel having a hole, means for rotatably mounting the drive wheels of each line, a plurality of lines of printing bands engaged with the wheels for printing a plurality of lines of data, an axially shiftable and rotatable selector shaft movable into the wheel holes of each line for selectively advancing any printing band, each shaft having a non-circular portion, a manually engageable knob for rotating and for axially shifting each shaft, each knob being non-rotatably mounted relative to the related selector shaft, adjacent knobs being relatively close to each other in certain axial positions, each knob having a non-circular portion engaged with a respective non-circular shaft portion to enable the knob to rotate the shaft, each knob being axially slidably mounted on the respective shaft to enable any knob to be shifted axially outward relative to its shaft to a limited extent to reduce interference with any other knob.

7. A print head, comprising: a plurality of lines of drive wheels, each drive wheel having a hole, means for rotatably mounting the drive wheels of each line, a plurality of lines of printing bands engaged with the wheels for printing a plurality of lines of data, an axially shiftable and rotatable selector shaft movable into the wheel holes of each line for selectively advancing any printing band, a manually engageable knob for rotating and for axially shifting each shaft, adjacent knobs being relatively close to each other in certain axial positions, and a spline connection between each knob and its respective shaft for enabling the knob to be shifted axially relative to the shaft to a position where interference with any other knob is reduced.

8. A print head, comprising: a plurality of lines of drive wheels, each drive wheel having a hole, means including concave mounting surfaces for rotatably mounting the drive wheels of each line at their outer peripheries, a plurality of lines of printing bands engaged with the wheels for printing a plurality of lines of data, an axially shiftable and rotatable selector shaft movable into the wheel holes of each line for selectively advancing any printing band, a manually engageable knob mounted on each selector shaft for both rotating the selector shaft and axially shifting the selector shaft, each knob being non-rotatably mounted relative to the related selector shaft, adjacent knobs being relatively close to each other in certain axial positions, means providing a lost-motion connection between each knob and its respective selector shaft to enable the knob to be pulled outwardly in the axial direction relative to any other knob to reduce interference with the other knob, and means for limiting movement of each knob in the axial direction so that the knob can transmit axial motion to the respective selector shaft.

9. A print head, comprising: a plurality of lines of drive wheels, each drive wheel having a hole, means including concave mounting surfaces for rotatably mounting the drive wheels of each line at their outer peripheries, a plurality of lines of printing bands engaged with the wheels for printing a plurality of lines of data, an axially shiftable and rotatable selector shaft movable into the wheel holes of each line for selectively advancing any printing band, means carried by the shaft for indicating the printing band with which the shaft is engaged, each shaft having a non-circular portion, a manually engageable knob mounted on each selector shaft for both rotating the selector shaft and axially shifting the selector shaft, each knob being non-rotatably mounted relative to the related selector shaft, adjacent knobs being relatively close to each other in certain axial positions, each knob having a non-circular portion engaged with a respective non-circular shaft portion to enable the knob to rotate the shaft, each knob being axially slidably mounted on the respective shaft to enable any knob to be shifted axially outward relative to its shaft to reduce interference with any other knob, and means for limiting movement of each knob in the axial direction so that the knob can transmit axial motion to the respective selector shaft.

10. A print head, comprising: a plurality of lines of drive wheels, each drive wheel having a hole, means including concave mounting surfaces for rotatably mounting the drive wheels of each line at their outer peripheries, a plurality of lines of printing bands engaged with the wheels for printing a plurality of lines of data, an axially shiftable and rotatable selector shaft movable into the wheel holes of each line for selectively advancing any printing band, means carried by the shaft for indicating the printing band with which the shaft is engaged, a manually engageable knob mounted on each selector shaft for both rotating the selector shaft and axially shifting the selector shaft, adjacent knobs being relatively close to each other in certain axial positions, a spline connection between each knob and its respective shaft for enabling the knob to be shifted axially relative to the shaft to a position where interference with any other knob is reduced and for enabling each knob to rotate its respective selector shaft, and means for limiting movement of each knob in the axial direction so that the knob can transmit axial motion to the respective selector shaft.

* * * * *